United States Patent [19]

Goujon

[11] Plant 4,463

[45] Oct. 9, 1979

[54] ROSE UNDERSTOCK—FREDICA VARIETY

[75] Inventor: Claude Goujon, Versailles, France

[73] Assignee: Conard-Pyle Company, West Grove, Pa.

[21] Appl. No.: 939,259

[22] Filed: Sep. 5, 1978

[51] Int. Cl.[2] ..... A01H 5/00
[52] U.S. Cl. ..... Plt./1
[58] Field of Search ..... Plt./1

*Primary Examiner*—Robert E. Bagwill

*Attorney, Agent, or Firm*—Burns, Doane, Swecker & Mathis

[57] ABSTRACT

The invention relates to a new and distinct variety of rose plant which is particularly suited for use as an understock when growing rose plants in a greenhouse. The new variety is substantially thornless in nature, and is a product formed by the crossing of a *Rosa indica major* seed parent by a thornless male, *Rosa multiflora inermis.*

14 Drawing Figures

SUMMARY OF THE INVENTION

The object of the present invention is to provide a new variety of rose plant which is highly suited for use as an understock when growing rose plants in a greenhouse.

The original plant was produced in 1969 at the National Agronomic Institute for Research (i.e. Institut National de la Recherche Agronomique) of Versailles, France, by crossing a *Rosa indica major* seed parent by a thornless male, *Rosa multiflora inermis,* and is of the diploid type (2n=14).

As a result of this crossing I have produced a new and useful rose variety which is distinguished from its parents and all rose varieties of which I am aware by the following combination of characteristics:

(1) a substantially thornless nature (almost total absence of prickles), (2) a multiflorous inflorescence, (3) white flowers commonly of five petals each, (4) foliage similar to but more ample than that of *Rosa indica major,*

(5) good tolerance to diseases including powdery mildew, and (6) exceptional suitability for use as an understock for growing rose plants in a greenhouse.

Asexual reproduction of my new variety by cuttings shows that all characteristics of the new variety are established and transmitted through succeeding propagations.

The new variety has been found to produce usable cuttings for the production of an understock on a more consistent basis than *Rosa indica major.* The precocity of the new variety is slightly less than that of *Rosa indica major,* and much greater than that of *Rosa noisettiana manettii.*

Also, the present variety exhibits a perfect affinity with the tetraploid Hybrid Tea rose varieties grown in France. During the winter the number of flowers obtained in a greenhouse while employing this variety as an understock is in excess of that obtained when employing *Rosa indica major* and *Rosa noisettiana manettii* as the understock for all varieties forced. The stem length and flower color of such varieties grown on the present understock are identical to those formed on *Rosa indica major* and *Rosa noisettiana manettii.*

The rose plant of the new variety has been designated the Fredica variety.

BRIEF DESCRIPTION OF THE DRAWINGS

The accompanying photographs depict typical specimens of the vegetative growth and flowers of my new variety in color as nearly true as possible in a color illustration of this nature.

DETAILED DESCRIPTION

Figures 1, 2, 3, 4, 5, 6, 7, 8, 9, 10, 11, 12, 13, 14:
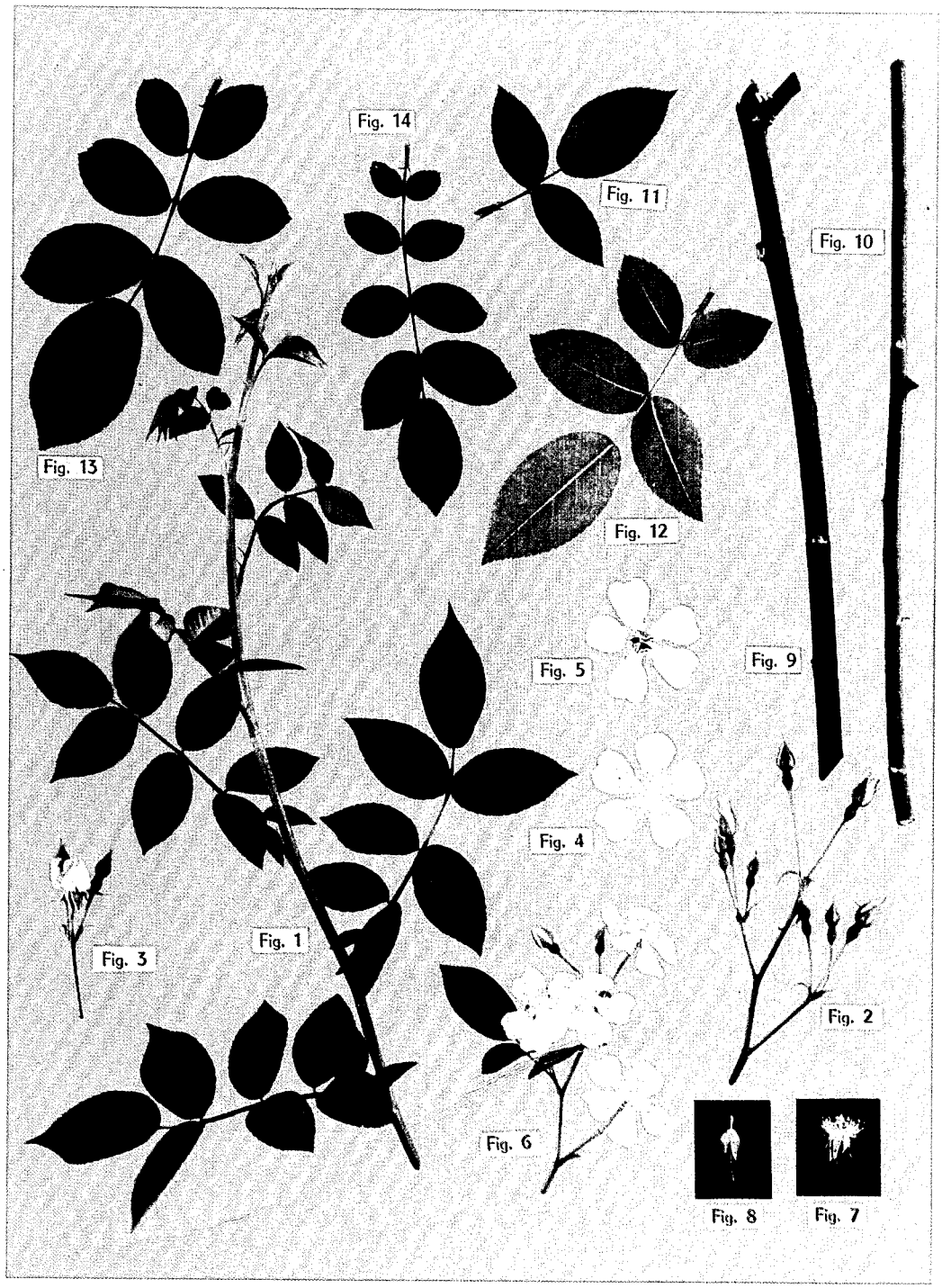
FIG. 1 is a specimen of a young shoot.
FIG. 2 is an inflorescence specimen showing young buds and buds as the sepals begin to open.
FIG. 3 is an inflorescence specimen wherein the opening of flower petals is in progress.
FIG. 4 is a specimen showing the inside of a fully open flower.
FIG. 5 is a specimen showing the outside of a fully open flower.
FIG. 6 is another inflorescence specimen showing fully opened flowers.
FIG. 7 is a specimen of a receptacle showing the arrangement of the stamens.
FIG. 8 is a specimen of a receptacle showing the arrangement of the pistils once the stamens have been removed.
FIG. 9 is a specimen which is a portion of a main branch.
Fig. 10 is a specimen which is a portion of a flowering stem.
FIG. 11 is a specimen of a 3-foliole leaf—upper surface.
FIG. 12 is a specimen of a 5-foliole leaf—upper surface.
FIG. 13 is a specimen of a 7-foliole leaf—upper surface.
FIG. 14 is a specimen of a 9-foliole leaf—upper surface.

The following is a detailed description of the characteristics of the new variety of rose plant. The chart used in the detailed identification of the petal colors is that of the Royal Horticultural Society (R.H.S. Colour Chart). In other instances general color terms are used in accordance with their ordinary dictionary significance.

Growth habit: Upright to bushy. More ample foliage than that of *Rosa multiflora inermis* which also exhibits an upright to bushy growth habit. More bushy growth habit than that of *Rosa indica major* which tends to be upright.

Stem:

*Color of young shoots.*—Light green.

*Color of flowering branches (at first blooming).*—Light green to reddish purple.

*Bloom on stems (at first blossoming).*—Very thin.

Prickles (at about the third of the flowering branches):

*Number.*—Practically non-existent.

*Maximum length.*—About 5 millimeters.

*Maximum length at base.*—About 5 millimeters.

*Width of base.*—Narrow.

*Mark at base.*—Oboval.

*Shape of the upper edge.*—Straight.

*Shape of the lower edge.*—Slightly concave.

*Color.*—Reddish purple.

Composite leaf (typical leaf of a medium ⅓ of a flowering branch):

*Length (petiole included).*—About 123 millimeters.

*Maximum width.*—About 84 millimeters.

*Length of petiole (to first pair of leaflets).*—About 30 millimeters.

*Angle of petiole to stem.*—About 45° to 90°.

*Number of leaflets (terminal leaflet included).*—3 to 9, commonly 7.

*Overlapping of the leaflets.*—None.

*Ratio length:width.*—About 1.46:1.

*Color of young leaves.*—Reddish purple.

*Color of adult leaves.*—Dark green.

Leaflets (first pair starting at terminal end):

*Shape of tip.*—Narrow point.

*Symmetry of tip.*—Symmetrical.

*Symmetry of base.*—Symmetrical.

*Shape of base.*—Rounded.

*Type of denticulation of edge.*—Single.

*Mode of denticulation of edge.*—Very fine.

*Structure of upper surface.*—Smooth, hairless.

*Appearance of upper surface.*—Dull.

Terminal leaflet:

*Length.*—About 48 millimeters.

*Maximum width.*—About 28 millimeters.

*Length of petiole.*—About 18 millimeters.

*Ratio width composite leaf:width terminal leaflet.*—About 3.23:1.

*Ratio width terminal leaflet:length small petiole.*—About 2:1.

*Ratio length terminal leaflet:length composite leaf*.—About 0.39:1.

Stipule:

*Ratio length of stipule:length petiole.*—1:2.

*Shape.*—Very narrow with very fine teeth.

Flowering (at start of flowering on about 50% of plants one year after planting):

*Frequency.*—Blooms once.

*Number of blooms on each flowering branch.*—Average.

*Type.*—Single.

*Shape.*—Flattened cup.

*Diameter of flower.*—About 27 millimeters. Larger flower than *Rosa multiflora inermis* which is about 16 millimeters in diameter, and smaller flower than *Rosa indica major* which is about 50 millimeters in diameter.

*Fragrance.*—Nil.

*Number of petals.*—Commonly 5.

Floral peduncle (at dehiscence of the anthers):

*Habit.*—Erect.

*Anthocyanic pigmentation.*—Absent.

Petals:

*Ratio of length:width.*—>1:1.

*Shape.*—Ovoid.

*Color of center of upper surface.*—White 155A.

*Color of edge of upper surface.*—White 155A.

*Color of center of under surface.*—White 155A.

*Color of edge of under surface.*—White 155A.

*Tip.*—Not reflexed.

*Lateral edges.*—Not reflexed.

*Edges.*—Not waved.

Stamens (exterior):

*Color of filaments.*—White.

Styles:

*Length.*—Long.

*Color (upper half).*—Yellow green.

*Hairiness.*—Scanty.

Stigmas:

*Position in relation to anthers.*—Same level.

Receptacle:

*Width.*—Narrow.

*Shape.*—Jug-like.

*Fruit diameter.*—About 8 millimeters. Larger than fruit of *Rosa multiflora inermis* which is about 5 millimeters, and smaller than *Rosa indica major* which is about 10 millimeters.

I claim:

1. A new and distinct variety of rose plant produced by the crossing of a *Rosa indica major* seed parent by the thornless male, *Rosa multiflora inermis*, characterized particularly as to novelty by the unique combination of (a) a substantially thornless nature, (b) a multiflorous inflorescence, (c) white flowers commonly of five petals each, (d) foliage similar to but more ample than that of *Rosa indica major*, (e) good tolerance to diseases including powdery mildew, and (f) exceptional suitability for use as understock for growing rose plants in a greenhouse.

* * * * *